United States Patent
Miller (10) Patent No.: US 7,092,487 B2
(45) Date of Patent: Aug. 15, 2006

(54) X-RAY PALLET PROCESSING

(75) Inventor: Robert Bruce Miller, Albuquerque, NM (US)

(73) Assignee: The Titan Corporation, San Diego, CA (US)

( * ) Notice: Subject to any disclaimer, the term of this patent is extended or adjusted under 35 U.S.C. 154(b) by 238 days.

(21) Appl. No.: 10/681,756

(22) Filed: Oct. 8, 2003

(65) Prior Publication Data

US 2005/0078789 A1   Apr. 14, 2005

(51) Int. Cl.
*G21K 5/00* (2006.01)
(52) U.S. Cl. .......................................... 378/64; 378/69
(58) Field of Classification Search ................. 378/64, 378/68, 69, 119, 137, 138, 143; 250/492.1, 250/492.3
See application file for complete search history.

(56) References Cited

U.S. PATENT DOCUMENTS 6,504,398 B1   1/2003   Lien et al. .................... 326/41
6,504,898 B1   1/2003   Kotler et al. .................. 378/64
6,931,095 B1 *  8/2005   Koenck et al. ............... 378/64

\* cited by examiner

*Primary Examiner*—Courtney Thomas
(74) *Attorney, Agent, or Firm*—Peter K. Hahn; Luce, Forward, Hamilton & Scripps (57) ABSTRACT

This invention is advantageous in irradiating pallets which cannot be irradiated by conventional techniques, even by x-rays, throughout their complete volumes. In one embodiment, a scan horn scans electron beamlets through a sweep angle. A dipole bends the electron beamlets to focus the electron beamlets at the pallet center. After being bent, the beam becomes converted to x-rays which are irradiated through the pallet to the pallet center. During this irradiation, the pallet is moved in a direction substantially perpendicular to the irradiation. In this way, a quarter of the pallet is irradiated. When the quadrant radiation is completed, the radiation is interrupted and the pallet is rotated 90° to have a second side of the pallet face the radiation. The operation is sequentially repeated for each of the pallet sides. The four (4) irradiated quadrants define the pallet's complete cross-sectional area.

35 Claims, 5 Drawing Sheets

X-RAY PALLET PROCESSING

This invention relates to a system for, and method of, irradiating pallets. The invention is particularly adapted to irradiate pallets which are so thick that they cannot be irradiated by conventional techniques even when x-rays are used to provide the irradiation.

BACKGROUND OF THE INVENTION

It has been known for some time that drugs and medical instruments and other implements have to be irradiated so that they will not cause patients to become ill from harmful bacteria when they are applied to the patients. Systems have accordingly been provided for irradiating drugs and medical instruments and other implements. The drugs and the medical instruments and other implements have then been stored in sterilized packages until they have been ready to be used.

In recent years, it has been discovered that foods can carry harmful bacteria if they are not processed properly or, even if they are processed properly, that the foods can harbor and foster the proliferation of such harmful bacteria if they are not stored properly or retained under proper environmental conditions such as temperature. Some of the harmful bacteria can even be deadly.

For example, harmful bacteria have been discovered in recent years in hamburgers prepared by one of the large hamburger chains. Such harmful bacteria have caused a number of purchasers of hamburgers at stores in the chain to become sick. As a result of this incident and several other similar incidents, it is now recommended that hamburgers should be cooked to a well done, or at least a medium, state rather than a medium rare or rare state. Similarly, harmful bacteria have been found to exist in many chickens that are sold to the public. As a result of a number of incidents which have recently occurred, it is now recommended that all chickens should be cooked until no blood is visible in the cooked chickens.

To prevent incidents such as discussed in the previous paragraphs from occurring, various industries have now started to irradiate foods before the foods are sold to the public. This is true, for example, of hamburgers and chickens. It is also true of fruits, particularly fruits which are imported into the United States from foreign countries. The fruit is irradiated to disinfect the fruit and rid the fruit of insects and fleas.

In previous years, gamma rays have generally been the preferred medium for irradiating various articles. The gamma rays have been obtained from a suitable material such as cobalt and have been directed to the articles to be irradiated. The use of gamma rays has had certain disadvantages. One disadvantage is that irradiation by gamma rays is slow. Another disadvantage is that irradiation by gamma rays is not precise. This results in part from the fact that the strength of the source (e.g. cobalt) of the gamma rays decreases over a period of time and that the gamma rays cannot be directed in a sharp beam to the articles to be irradiated. This prevents all of the gamma rays from being useful in irradiating the articles.

In recent years, electron beams have been directed to articles to irradiate the articles. Electron beams have certain advantages over the use of gamma rays to irradiate articles. One advantage is that irradiation by electron beams is fast. For example, a hamburger patty having a square cross section can be instantaneously irradiated by a passage of an electron beam of a particular intensity through the hamburger patty. Another advantage is that irradiation by an electron beam is relatively precise because the strength of the electron beam remains substantially constant even when the electron beam continues to be generated over a long period of time. A further advantage is that the space occupied by the electrons and the direction of movement of the electrons can be precisely controlled since the electrons are in the form of a beam. A disadvantage is that the electrons can penetrate an article through only a limited distance. To increase the distance of penetration of the article, the electron beams can be directed to opposite sides of the article.

X-rays have also been used to irradiate articles. The x-rays may be formed from electron beams. An advantage in irradiating articles with x-rays is that the x-rays can irradiate articles which are thicker than the articles which are irradiated by electron beams. However, it would also be desirable to irradiate articles with x-rays from opposite sides of the articles to enhance the uniformity of the absorbed x-ray energy within the articles and to enhance the efficiency with which the x-ray energy is absorbed by the articles. Application Ser. No. 10/224,062 filed by me on Aug. 20, 2002 for a System For and Method of Irradiating Opposite Sides of an Article and assigned of record to the assignee of record of this application discloses and claims a system for irradiating articles with x-rays at opposite sides of the article by using only a single source of irradiation.

By using a single source of x-rays to irradiate opposite sides of the article, the radiant energy at the opposite sides of the article are substantially identical so that each of the opposite sides of the article receives substantially identical patterns of radiation. Furthermore, the costs are minimized since accelerators are quite expensive.

Sometimes the articles to be irradiated are so thick that the central portion of the article cannot be properly irradiated even when the articles are irradiated with x-rays from opposite sides of the articles. For example, this is true of dense food stuffs. In such instances, the minimum required dose cannot be provided at the center of the pallet without overdosing the outer regions of the pallet.

DETAILED DESCRIPTION OF PREFERRED EMBODIMENTS OF THE INVENTION

Figure 3:
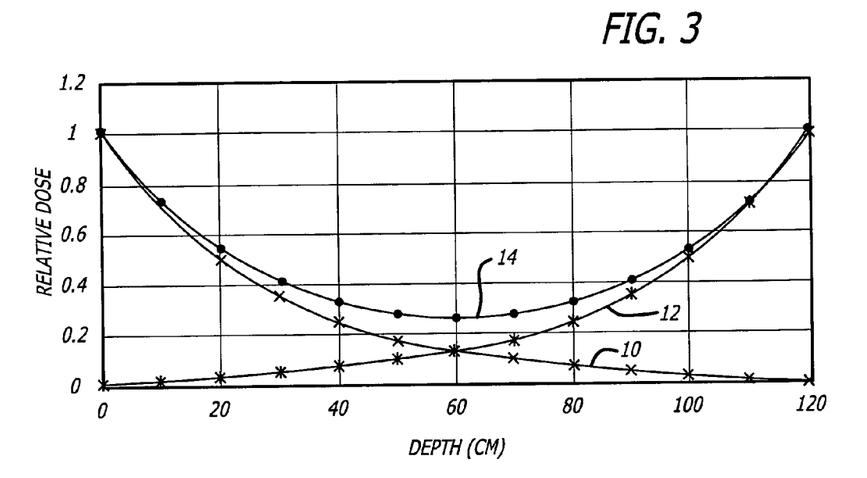
FIG. 3 is a curve showing the relative doses of irradiation received by a pallet at different depths in the pallet when radiation is applied to the pallet from opposite sides of the pallet.

FIG. 3 provides curves showing the depth along the horizontal axis of an irradiated article. The article may be a food pallet having an average density of about 0.5 g/cm3 where g indicates grams and cm indicates centimeters. This depth is shown as being between zero (0) centimeters and one hundred and twenty (120) centimeters. The curve in FIG. 3 shows relative doses of radiation along the vertical axis. The relative doses vary between values of 0 and 1 depending upon the depth through which the radiation penetrates. As will be seen, the relative doses progressively decrease as the radiation penetrates into the article from one side of the article.

A curve 10 is provided in FIG. 3 when the radiation penetrates into an article from a zero (0) position to a position of 120 centimeters. A curve 12 is provided in FIG. 3 when the radiation penetrates into the article from a position of 120 centimeters to a position of zero (0) centimeters. As will be seen, the curve 12 is inverse to the curve 10.

A curve 14 is provided in FIG. 3 when the curves 10 and 12 are combined—in other words, when radiation passes into the article from opposite sides of the article. As will be seen in FIG. 3, at an intermediate position of sixty centimeters (60 cm) in the depth of the article, the relative dose of radiation is approximately twenty five percent (25%) of the radiation dose at the opposite ends of the article. In other words, the ratio of the maximum dose in the article to the minimum dose in the article is approximately 4:1.

Figure 4:
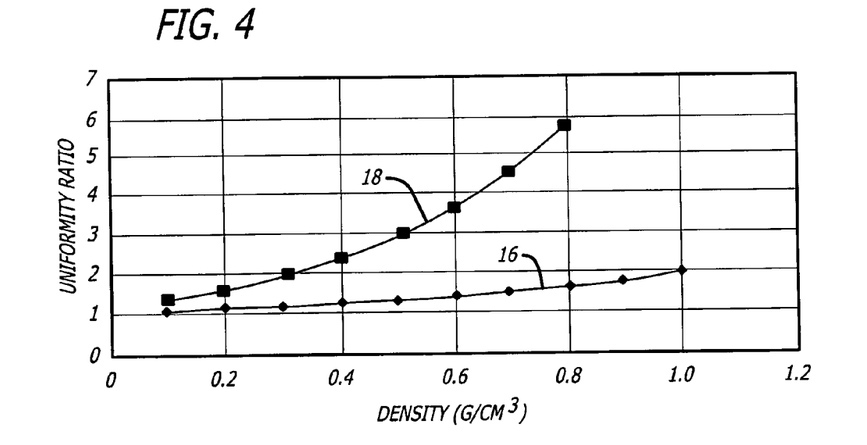
FIG. 4 is a curve showing the density of a pallet along a horizontal axis and the ratio between the maximum and minimum intensities of irradiation in the pallet along a vertical axis.

FIG. 4 provides a curve indicating the relationship between article density and the maximum/minimum ratio of radiation intensity in the article. The article density is indicated in the horizontal direction in grams per centimeters cubed (g/cm3). The maximum/minimum ratio (or uniformity ratio) is indicated in the vertical direction. Two (2) curves respectively indicated at 16 and 18 are provided in FIG. 4. The curve 16 is provided for an eighteen inch (18") pallet and the curve 18 is provided for a forty inch (40") pallet.

As will be seen, a maximum/minimum ratio of at least approximately 2 is provided for the 18" carrier for densities up to 1 gm/cm3. This provides for an excellent irradiation of articles such as containers of spices. The mass throughput efficiencies for these articles can be in the range of 0.03–0.035.

Pallets of produce having average densities of 0.4 g/cm3 or less can also be processed effectively. However, for food products with higher densities, the maximum/minimum ratio increases to an excessive value. For example, the variation of the radiation dose with different depths for approximately a 48" pallet having an average density of 0.5 g/cm3 is shown in FIG. 3. As will be seen, the maximum/minimum ratio in the curve 14 for such a pallet is approximately 4. However, when ground beef products having a density of 0.9 g/cm3 and requiring a maximum/minimum ratio of 1.5 or less are irradiated, the maximum/minimum ratio should be 1.5 or less.

U.S. Pat. No. 6,504,898 was issued by the United States Patent Office to Jim Kotler and Joseph Boroa on Jan. 7, 2003 for a Product Irradiator for Optimizing Dose Uniformity in Products. A simplified version of the system disclosed and claimed in U.S. Pat. No. 6,504,898 is generally indicated at 20 in FIG. 1. It includes a scan horn 22, a collimator 24 and a rotating pallet 26. The scan horn 22 scans an x-ray beam 28 in a vertical direction. The scanned beam is collimated as in a horizontal direction indicated at 29 and passes to the pallet 26. The pallet 26 continuously rotates through a revolution and the scan horn 22 passes radiation continuously to the pallet as the pallet rotates. The pallet 26 rotates at a variable rate dependent upon the rotating position of the pallet. The variable rate of rotation is provided because the distance between the collimator 24 and the pallet 26 varies as the pallet rotates. The variable rate of rotation of the pallet 26 complicates the construction and operation of the system shown in FIG. 1.

Figure 1:
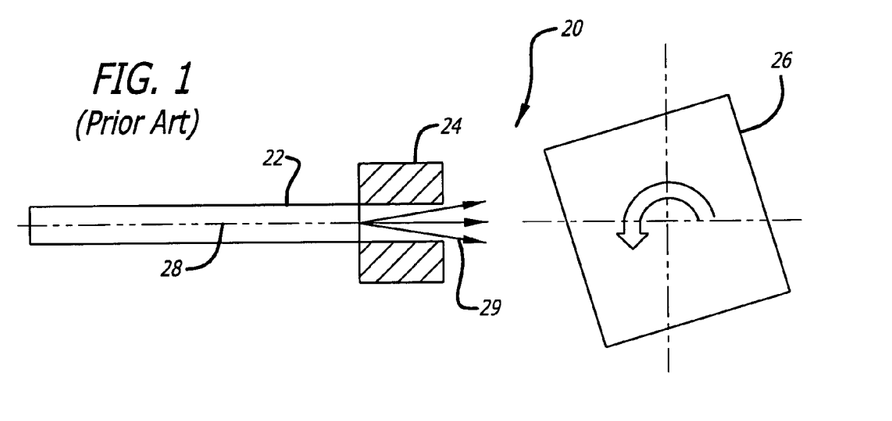
FIG. 1 is a schematic sectional view showing a system of the prior art for irradiating a relatively thick pallet with x-rays.

Key features of the system shown in FIG. 1 and described in the previous paragraph include time dependent rotation of the pallet 26 plus collimation of the x-ray radiation for products of the highest density. The collimation prevents x-rays emitted at large angles from reaching the pallet 26. This decreases the surface dose enhancement and effectively improves the penetration depth. Using this approach, the patentees in U.S. Pat. No. 6,504,398 claim to have achieved maximum/minimum ratios of 1.5 or less for products having average densities to 0.9 g/cm3. However, the mass throughput efficiency decreases at the higher densities to about 2% because of the use of collimation.

Figure 2:
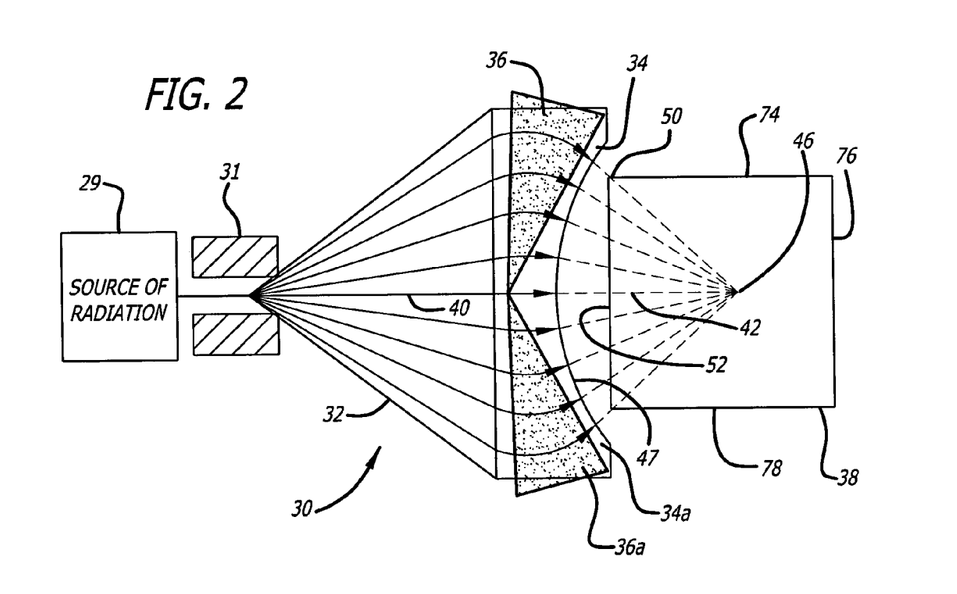
FIG. 2 is a schematic sectional view showing a system constituting a preferred embodiment of this invention for irradiating a relatively thick pallet.

FIG. 2 shows a system, generally indicated at 30, which constitutes a preferred embodiment of the invention. The system 30 includes an electron source 29, a scanning magnet 31, a scan horn 32 and a variable strength dipole magnet 36. The scan magnet 31 deflects electron beamlets from the source 29 in a horizontal plane through a suitable angle such as approximately 20° on each side of a median line 40. The beamlets then pass through the scan horn 32 to the variable dipole magnet 36 which is indicated in FIG. 2 by a speckled configuration.

The variable dipole magnet 36 bends the electron beamlets 33 so that they extend in a radial path (indicated by broken lines at 42) through the pallet toward a focal point 46. The focal point 46 is at the center of the pallet 38 in a horizontal section of the pallet. Before they reach the pallet 38, the electron beamlets reach a converter 34 which converts the beamlets to x-rays and directs the x-rays to the focal point 46. The converter 34 may have a curved configuration. A collimator may be disposed between the converter 34 and the front side of the pallet 38 to collimate the x-rays in a vertical direction. The region of collimation is shown as 43 in FIG. 5.

The pallet 38 may have a largely square configuration in horizontal section. The pallet 38 is disposed so that one of the sides of the pallet directly faces the magnetic lens. The x-rays exit the converter 34 in a radial direction at the rear end of the converter. At one extremity, the radiation passes through a position 50 defining extremity of a side 52 of the pallet. At the other extremity, the radiation passes through an extension of the median line 40. In this way, a portion constituting one eighth of the sectional area of the pallet 38 is irradiated.

Figure 5:
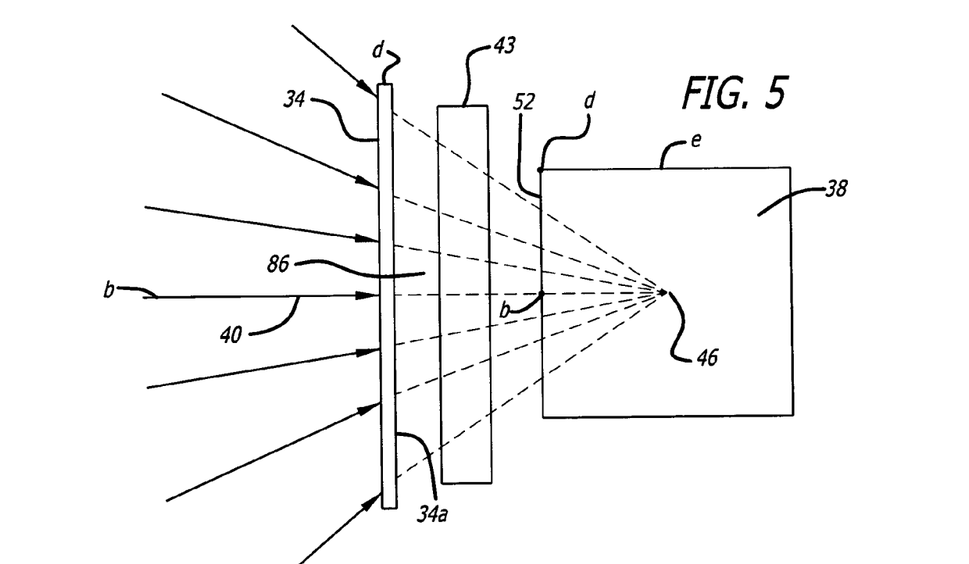
FIG. 5 is a schematic diagram showing the irradiations applied to a pallet at different positions in the pallet by the system shown in FIG. 2.

Another one eighth of the cross sectional area of the pallet 38 may be irradiated at the same time by a magnetic lens disposed below the magnet lens defined above and including a scan horn 32a, and a variable magnetic dipole 36a. A converter 34a is provided to convert electron beamlets to x-rays which are directed to the focal point 46. The converters 34 and 34a may have substantially identical configurations as shown in FIG. 2. Alternatively, the converters 34 and 34a may have substantially planar configurations as shown in FIG. 5.

Figure 8:
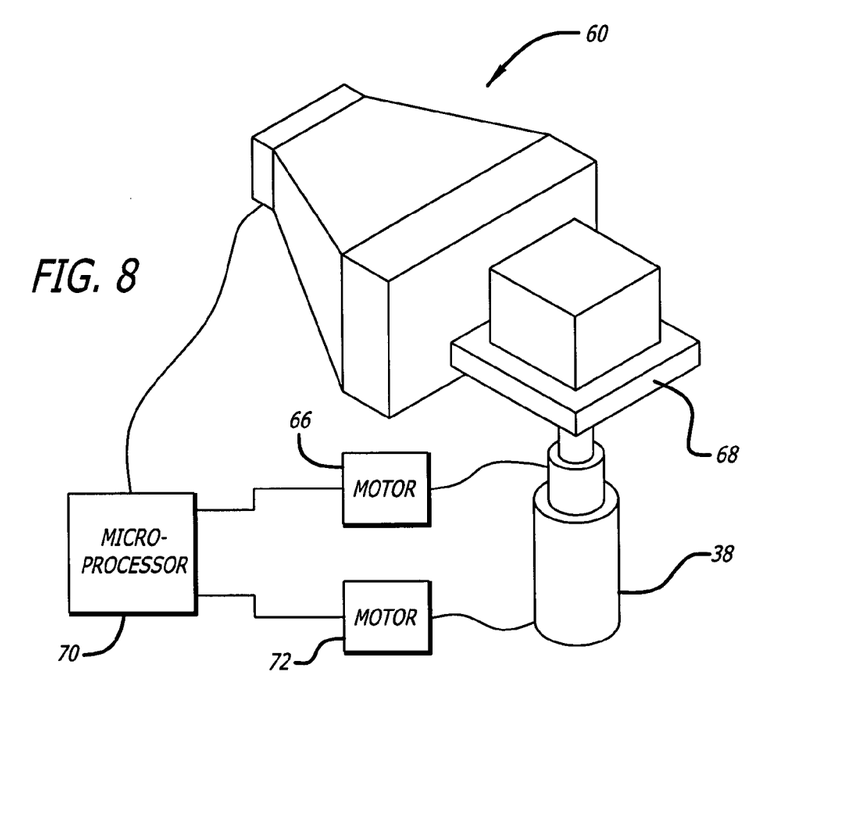
FIG. 8 is a schematic perspective view showing a system for providing sequences of (1) alternately energizing a radiation source while moving the pallet axially and (2) rotating the pallet through an angle of 90° while interrupting the radiation and holding the pallet stationary in an axial direction.

A system generally indicated at 60 in FIG. 8 is provided for irradiating the full volume of the pallet 38. As previously indicated, the first quarter of the pallet 38 as defined by the side 52 and the focal position 46 is initially irradiated. During this time, the pallet 38 is moved downwardly into the plane of the paper as by a motor 66 so that successive positions in the axial direction of the pallet become irradiated. The vertical downward movement of the pallet is controlled by a microprocessor 70. The pallet may be disposed on a holder 68 in the downward movement of the pallet into the plane of the paper. During this time, the pallet 38 is not rotated and the pallet is irradiated.

When the pallet 38 reaches an extreme position corresponding to the vertical end of the pallet 38, the microprocessor 70 causes the downward movement of the pallet to be terminated. The microprocessor 70 then activates a motor 72 which rotates the pallet through an angle of substantially 90° so that a side 74 of the pallet faces the magnetic lens and the converter 34. The rotation of the pallet 38 is on an axis corresponding to the direction of movement of the pallet into and out of the plane of the paper. During this time, the radiation from the magnetic lens may be interrupted. Instead of interrupting the radiation from the magnetic lens, the pallet may be moved out of the radiation field before being rotated through the angle of substantially 90°.

After the pallet 38 has been rotated through the angle of 90°, the application of radiation to the pallet is resumed under the control of the microprocessor 70. At the same time, a vertical movement of the pallet 38 upwardly out of the plane of the paper is initiated. In this way, a second quadrant defined in the pallet 38 by the pallet side 74 and the focal position 46 is irradiated.

The sequences described above are repeated to irradiate the quadrants defined by each of sides 76 and 78 and the focal position 46 of the pallet 38. In this way, the complete volume of the pallet 38 is irradiated in two (2) round trips of the pallet 38 into and out of the plane of the paper. Every position in the pallet 38 is accordingly irradiated because the four (4) quadrants have the common focal position 46.

Figure 7:
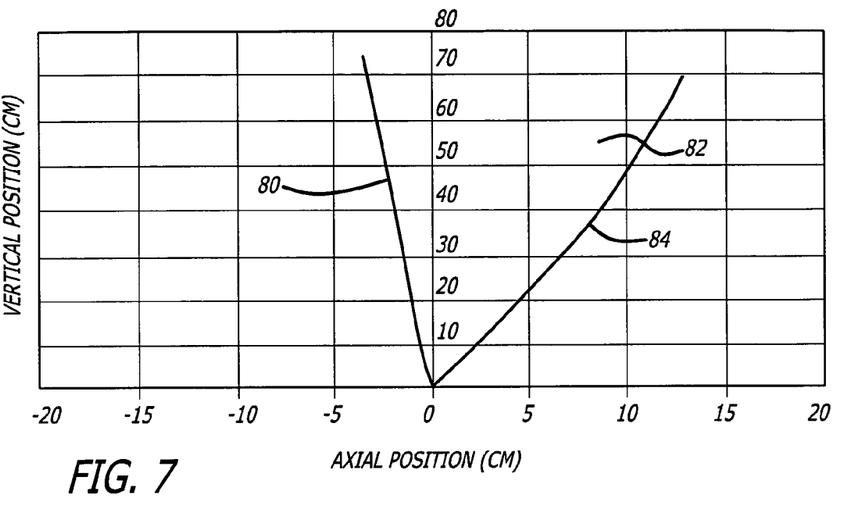
FIG. 7 is a two-dimensional view of the configuration of a dipole magnet included in the embodiment of the invention shown in FIG. 2.

The variable dipole magnet 36 can have a shape as shown in FIG. 7 and as described below. The front part of the dipole magnet 36 can be considered as a lens which causes all electron trajectories to become parallel. As indicated in FIG. 7, the front edge 80 of the dipole magnet 36 can define substantially a straight lens. The rear or exit portion 82 of the dipole magnet 36 can be considered to be a lens which focuses all trajectories of the radiation at the focal position 46 in the pallet. As will be seen in FIG. 7, the rear edge 84 of the dipole magnet 36 deviates slightly from a straight line to have a slightly convex configuration.

The approximate shape of the dipole magnet 36 for focusing all beam trajectories at the center 46 of the pallet 38 is shown in FIG. 7 when the pallet 38 has a square configuration with each side having a length of approximately one hundred and twenty centimeters (120 cm). In this configuration, an air gap 86 (FIG. 5) of approximately ten centimeters (10 cm) may be provided between the rear edge of the converter 34 and the side of the pallet 38 closest to the converter.

For example, neglecting fringe field effects, the shape of the variable dipole magnet 36 may be as shown in FIG. 7 for a 5-MeV beam, a maximum scan angle of +/−11.25 degrees, a product foot print of 120 cm by 120 cm, a 10 cm air gap and an assumed field strength of 1 KG (giving a radius of curvature of about 18 cm). As will be seen and as previously indicated, the angle of the entrance face 80 of the dipole magnet 36 is nearly constant at progressive positions along the entrance face but the angle of the exit face 84 of the dipole magnet is not constant at progressive positions along the exit face.

The maximum excursion of an electron having the maximum scan angle is about seventy five centimeters (75 cm) from the mid-plane. Thus, the total length (in the identical direction in FIGS. 2 and 7) of the modified bowtie dipole magnet 36 will be of the order of two meters (2 m). With the shallow scan angle shown in FIG. 2 for the scan horn 32, the scan horn is relatively long (about four (4) meters). An increased scan angle will decrease the length of the scan horn 32 without appreciably changing the length of the dipole magnet 36. However, the front face of the dipole magnet 36 will have a different angle.

An analytical x-ray model has been provided to analyze the performance of the system shown in FIGS. 2 and 8 and described above. The specific configuration of the calculation is shown in FIG. 5. The air gap distance between the converter 34 and the pallet 38 has been assumed to be ten centimeters (10 cm) and the pallet dimensions have been assumed to be ten centimeters (10 cm) by ten centimeters (10 cm). No collimation has been used. The electron intensity has been assumed to be uniform at the converter 34. However, the incidence angle has been assumed to vary linearly from zero at the mid-plane 40 (FIG. 5) to a maximum of +/−45 degrees at the extremes of the scan (−/+70 cm).

With no collimation, there is some surface dose enhancement. Furthermore, the maximum/minimum ratio has improved from approximately 4 as shown in the curve 18 in FIG. 4 to about 1.6. This is a rather dramatic improvement. With higher densities, however, collimation as shown in FIG. 2 may be desirable to achieve a maximum/minimum ratio less than 2. However, collimation would be at the expense of mass throughput efficiency.

Figure 6:
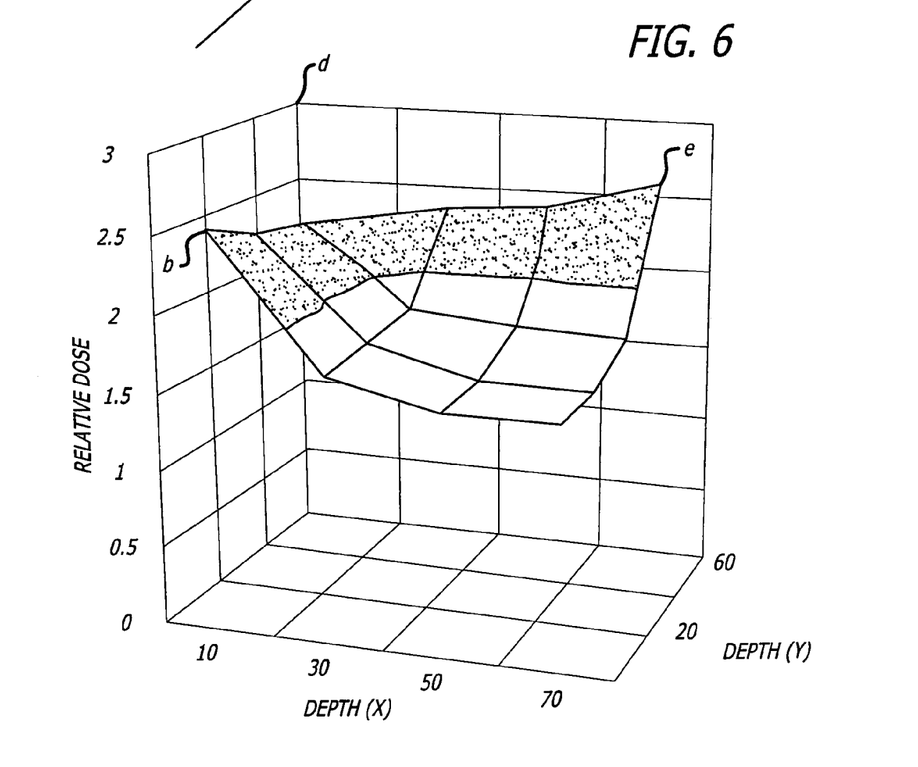
FIG. 6 is a schematic representation in three (3) dimensions of the dose distribution provided in a pallet by the system shown in FIG. 2.

FIG. 6 illustrates dose distribution in a quadrant of the pallet 38 with a symmetric, four-side irradiation using the configuration of FIG. 5. For a substantially uniform density of 0.5 g/cm3, the maximum/minimum ratio is about 1.6 even without collimation. Certain positions in FIG. 6 correspond to certain positions in FIG. 5. These are indicated at b in FIGS. 5 and 6, at d in FIGS. 5 and 6, and at e in FIGS. 5 and 6.

Figure 9:
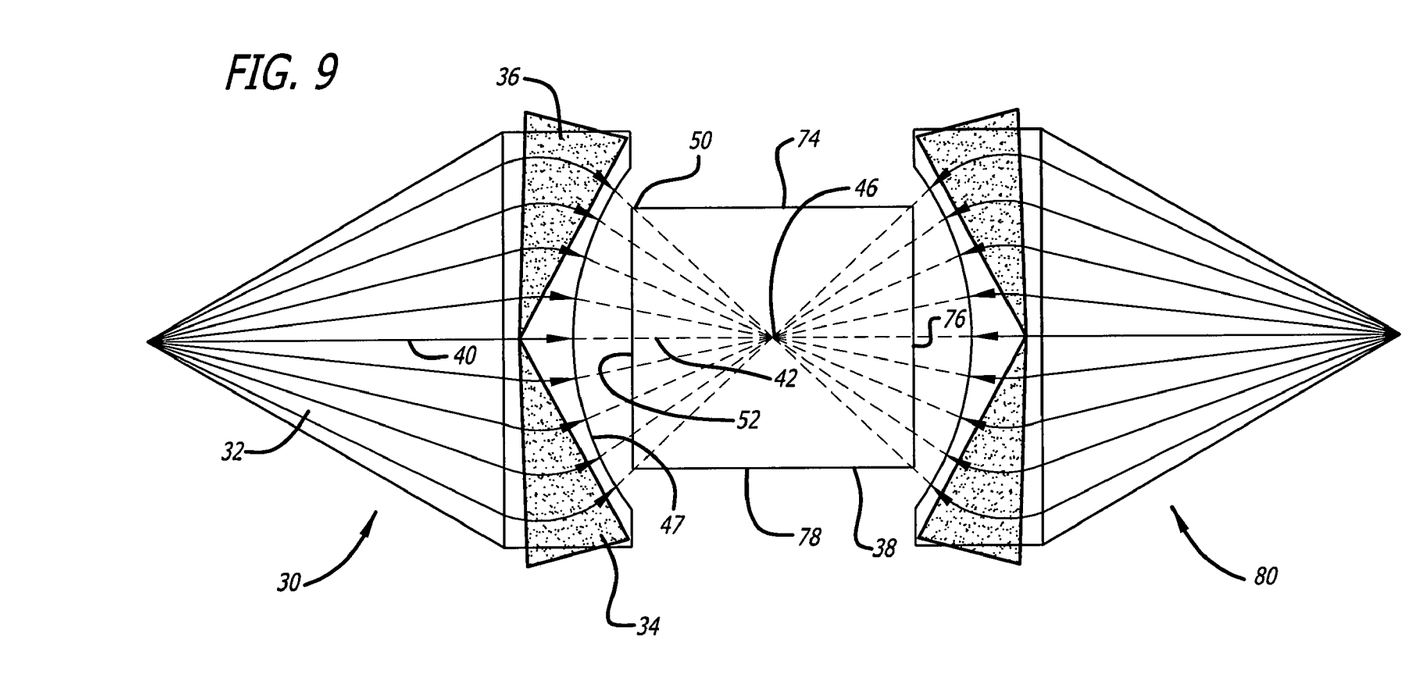
FIG. 9 is a schematic sectional view of a system which employs two (2) of the systems shown in FIG. 2 and disposes each of the systems at an opposite side of a pallet from the other system.

FIG. 9 indicates a system employing two (2) of the systems shown in FIGS. 2 and 8. The system shown in FIGS. 2 and 8 is generally indicated at 30 and the other system is generally indicated at 80. The system 80 corresponds in construction to the system 30. The system 80 is disposed on the opposite side of the pallet 38 from the system 30. The system 80 irradiates the pallet 38 on the opposite side of the pallet from the side irradiated by the system 30. The systems 30 and 80 irradiate the opposite sides of the pallet 38 during the axially downward movement of the pallet into the paper. The pallet 38 is then rotated through an angle of 90° with the radiation interrupted and without any axial movement of the pallet. The pallet 38 is then moved axially upwardly out of the plane of the paper with the radiation applied to the pallet. In this way, the four (4) quadrants of the pallet 38 are irradiated in a single round trip of the pallet in a direction perpendicular to the plane of the paper.

Although this invention has been disclosed and illustrated with reference to particular preferred embodiments, the principles involved are susceptible for use in numerous other embodiments which will be apparent to persons of ordinary skill in the art. The invention is, therefore, to be limited only as indicated by the scope of the appended claims.

What is claimed is:

1. A system for irradiating a pallet, comprising:
a source of radiation having first and second states for directing the radiation in a first plane toward the pallet in the first state and for not directing radiation toward the pallet by being de-energized in the second state,
a holder having first and second states for moving the pallet in a second plane substantially perpendicular to the first plane during the first state of the source and for preventing any movement of the pallet in the second state of the source, and
a motor having first and second states of operation for rotating the pallet on an axis substantially corresponding to the second plane during the second state of the source of radiation,
wherein the motor rotates the pallet through a particular angle each time that the source of radiation and the holder are in the second state.

2. The system set forth in claim 1, the source of radiation providing x-rays.

3. The system set forth in claim 1, a magnetic lens assembly for converging the radiation from the source at a particular position in the pallet during the first state of the source of radiation.

4. The system set forth in claim 3 wherein the motor is operable to rotate the pallet on the particular axis during the second state of the source of radiation and the holder.

5. The system set forth in claim 3 wherein the magnetic lens assembly converges the radiation from the source at the particular position on the pallet after each successive rotation of the pallet on the particular axis.

6. The system set forth in claim 5 wherein the source of radiation provides x-rays.

7. A system for irradiating a pallet, comprising:
a source of radiation for producing radiation in a first direction,
a converter configured to convert the radiation to x-rays that includes a concave rear surface, and
a magnetic lens for focusing the radiation at a particular position in the pallet in a direction different from the first direction.

8. The system set forth in claim 7 wherein the magnetic lens focuses the radiation at a center of the pallet.

9. The system set forth in claim 7 wherein the converter converges the x-rays to focus the converging x-rays at a center of the pallet.

10. The system set forth in claim 9 wherein the radiation initially constitutes electron beamlets and wherein the electron beamlets are converted to x-rays before the electron beamlets reach the pallet.

11. The system set forth in claim 10 wherein the magnetic lens includes a scan horn and a dipole magnet for producing electron beamlets and for bending the electron beamlets to focus the electron beamlet at a particular position in the pallet and focuses the x-rays at the particular position in the pallet.

12. The system set forth in claim 7 wherein the magnetic lens irradiates approximately one eighth of the cross sectional area of the pallet, the irradiated eighth being defined by lines extending radially from one extremity of the side of the pallet and a median position in the side of the pallet.

13. A system for irradiating a pallet, comprising:
a source of radiation having energized and de-energized states, magnetic members for focusing the radiation from the source on the center of the pallet, with the pallet non-rotary, to irradiate a first portion of the pallet,
a control for energizing the source of radiation, and
a drive member for rotating the pallet through a particular angle, with the source of radiation not being energized, after the irradiation of the first portion of the pallet, the source of radiation being thereafter operative to energize another portion of the pallet, with the pallet non-rotary, and to focus the radiation from the source toward the center of the pallet.

14. The system set forth in claim 13 wherein the source of radiation provides x-rays.

15. The system set forth in claim 13 wherein the pallet is rotatable on a particular axis and wherein the pallet is rotatable on the particular axis after the energizing of the pallet by the radiation from the source.

16. A system for irradiating a pallet having a plurality of sides, comprising:
a source of radiation having energized and de-energized states, and
a scan horn and a dipole magnet constructed and disposed relative to each other to irradiate, with the radiation from the source, a portion of the pallet;
wherein the pallet is not rotated when the source of radiation is in the energized state.

17. The system set forth in claim 16 wherein the radiation is provided in a particular plane and wherein a member is provided for rotating the pallet on an axis substantially perpendicular to the plane of the radiation.

18. The system set forth in claim 16 wherein the radiation is provided in a particular plane and wherein a member is provided for moving the pallet in a direction substantially perpendicular to the plane of the radiation during the time that the pallet receives the radiation from the source.

19. The system set forth in claim 18 wherein a member is provided for rotating the pallet on an axis substantially perpendicular to the plane of the radiation during the time that the pallet is not receiving radiation from the source.

20. The system set forth in claim 19 wherein a control system provides for
(a) the passage of radiation to the pallet during a first period and the movement of the pallet in the substantially perpendicular direction, without any rotation of the pallet, during the first period,
(b) the rotation of the pallet in a second period of time after the first period of time without any passage of radiation to the pallet and without any movement of the pallet in the perpendicular direction and without the passage of radiation to the pallet, and
(c) the passage of radiation to the pallet and the movement of the pallet in the substantially perpendicular direction, without any rotation of the pallet, during a third period of time after the second period of time.

21. The system set forth in claim 20 wherein the radiation from the source irradiates a first eighth of the volume of the pallet during the first period and a second eighth of the volume of the pallet different from the first eighth during the third period and wherein the first and second eighths of the pallets extend from different extremities of the pallet to the center of the pallet.

22. A system for irradiating a pallet, comprising:
a source of radiation,
magnetic members constructed and disposed relative to one another for bending the radiation from the source to pass through one side of the pallet to a focused position on the pallet,
a first member for rotating the pallet relative to the magnetic members,
a converter configured to convert the radiation to x-rays that includes a concave rear surface, and
a control system for initially providing for a radiation from the source to the pallet without any rotation of the pallet, then for a rotation of the pallet relative to the magnetic members and then for another radiation from the radiation source to the pallet without any rotation of the pallet.

23. The system set forth in claim 22 wherein a converter is provided for converting the radiation to x-rays.

24. The system set forth in claim 22 wherein the focused position is at the center of the pallet and wherein radiation is not directed from the source to the pallet while the pallet is rotating.

25. The system set forth in claim 22 wherein the source of radiation provides electron beamlets and wherein the converter directs the x-rays to the focused position on the pallet.

26. The system set forth in claim 22 wherein the focused position is at the center of the pallet and wherein radiation is not directed from the source to the pallet while the pallet is rotating and wherein the source of radiation provides electron beamlets and wherein the converter directs the x-rays to the focused position on the pallets.

27. A method of irradiating a pallet, comprising the steps of:
energizing a source of radiation;
directing radiation in a first plane from the source to the pallet,
providing a magnetic lens to focus the radiation in the first plane at a central position in the pallet while the radiation is directed to the pallet, and
moving the pallet past the radiation in a direction substantially perpendicular to the first plane during the direction of the radiation from the source to the pallet;
de-energizing the source of radiation after the pallet has moved in the direction substantially perpendicular to the first plane, and
rotating the pallet on an axis extending in the first plane through the pallet while the source is de-energized.

28. The method as set forth in claim 27 wherein the pallet is rotated through an angle of substantially 90° on an axis extending in the first direction through the center of the pallet while radiation from the source is de-energized.

29. The method as set forth in claim 27 wherein the radiation constitutes x-rays.

30. The method as set forth in claim 27 wherein the radiation is directed in a first direction in the first plane and wherein the radiation is scanned in the first plane and wherein the scanned radiation is thereafter converted to a radial direction in the pallet in the first plane and is focused at the center of the pallet.

31. The method as set forth in claim 27 wherein the pallet is rotated through an angle of 90° on an axis extending in the second direction through the pallet after the pallet has moved in the second direction substantially perpendicular to the first direction and wherein the radiation is interrupted during the rotation of the pallet and wherein the radiation constitutes x-rays and wherein the radiation is scanned in a second plane substantially perpendicular to the first plane and to the first direction and wherein the radiation is thereafter converted to a radial direction having a center at the center of the pallet.

32. A system, comprising:
a scan horn for scanning charged particles through a particular angle in a particular plane,
a dipole for bending the charged articles to extend in a particular direction through the pallet, and
a converter for converting the charged particles to x-rays and directing the x-rays in the particular direction through the pallet;
wherein the converter has a concave periphery and wherein the charged particles pass to the center of the pallet through the concave periphery in a direction substantially perpendicular to the concave periphery.

33. The system set forth in claim 32 wherein the converter directs the x-rays through the pallet in a radial direction converging at the center of the pallet.

34. The system set forth in claim 32 wherein an air gap is disposed between the concave periphery of the converter and the pallet.

35. The system set forth in claim 32 wherein the dipole varies the direction of the charged particles into a radial direction converging at the center of the pallet and wherein an air gap is disposed between the arcuate periphery of the converter and the pallet.

* * * * *